United States Patent
Daly

(10) Patent No.: US 6,571,799 B1
(45) Date of Patent: Jun. 3, 2003

(54) PROTECTIVE EYE SHADES FOR INFANTS AND METHOD OF EYE PROTECTION

(75) Inventor: Paul C. Daly, Abington, MA (US)

(73) Assignee: RIC Investments, Inc., Wilmington, DE (US)

( * ) Notice: Subject to any disclaimer, the term of this patent is extended or adjusted under 35 U.S.C. 154(b) by 0 days.

(21) Appl. No.: 09/670,782

(22) Filed: Sep. 27, 2000

(51) Int. Cl.[7] .................................................. A61F 11/00
(52) U.S. Cl. ............................. 128/857; 128/858; 2/15
(58) Field of Search ................................. 128/846, 857, 128/858; 2/15, 426, 427, 428, 431, 440, 445, 454

(56) References Cited

U.S. PATENT DOCUMENTS

| 3,895,397 | A | * | 7/1975 | Douglas ........................ 2/68 |
| 4,024,405 | A | | 5/1977 | Szot |
| 4,162,542 | A | | 7/1979 | Frank |
| 4,258,437 | A | | 3/1981 | Sawatsky |
| 4,411,263 | A | | 10/1983 | Cook |
| 4,502,476 | A | | 3/1985 | Welt |
| 4,644,588 | A | | 2/1987 | Zawacki |
| 4,790,031 | A | | 12/1988 | Duerer |
| 4,872,217 | A | | 10/1989 | Kitayama |
| 5,596,771 | A | | 1/1997 | Hsu et al. |
| 5,613,502 | A | | 3/1997 | Lee |
| 5,927,281 | A | | 7/1999 | Monteleone et al. |
| 5,940,886 | A | | 8/1999 | McCarthy Smith |

OTHER PUBLICATIONS

Small Beginnings, Photo–Therapy Mask, Jul. 19, 2000, 1 pg.
Bililight/Bili–mask, Wesley Medical Center, Jul. 12, 2000, 1 pg.
Photo–Mask, For Phototherapy, Jul. 12, 2000, 1 pg.
Robinson, Judith et al., *Letter to the Editor, Measurements of Light Transmission Through Phototherapy Eyeshields*, Clinical Pediatrics, Dec. 1990, p. 735.
Bill Mask, Olympic Phototherapy Products, Jun. 20, 2000, 1 pg.
Chin, K.C., et al., *Light Transmission of Phototherapy Eyeshields, Archives of Disease in Childhood*, 1987, pp. 970–971.
Robinson, Judith et al., *Light Transmission Measurements and Phototherapy Eyepatches*, Department of Ophthalmology, University of Birmingham Medical School, Jul. 30, 1990, 3 pgs.
Merenstein, Gerald B. et al., *Handbook of Neonatal Intensive Care, Fourth Edition*, Mosby, 1988, p. 406.
Cabana, Michael D. et al., *Phototherapy in Neonates*, The Pediatric Forum, Arch Pediatr Adolesc Med, vol. 152, Aug. 1988, p. 818.
Moseley, Merrick et al., *Letter to the Editor, Eye Protection During Phototherapy*, Acta Paediatr 82: 1993, p. 1042.
Moseley, H. et al., *Protective Light Shields for Neonatal Phototherapy*, The Lancet, Oct. 8, 1988, pp. 854–855.
Al–Salihi, Farouk L. et al., *Airway Obstruction by Displaced Eye Mask During Phototherapy*, Am J Dis Child—vol. 129, Nov. 1975, p. 1362.
Madsen, Lars P., *Short Commnuication, The Effectiveness of Eye Protection During High–Intensity Phototherapy*, Acta Paediatr 82: 91, 1993, 1 pg.

* cited by examiner

Primary Examiner—Michael A. Brown
(74) Attorney, Agent, or Firm—TraskBritt

(57) ABSTRACT

Protective eye shades for an infant comprising an outer sheath having two enlarged, oval segments connected by a narrower segment comprising a nose bridge and resilient eye rims secured to the enlarged oval segments and projecting from the outer sheath. The outer sheath may be secured over the infant's face using structure selected from the group consisting of adhesives, hydrocolloids, gels, nets and straps. A preferred bonnet structure for securing the eye shades is also disclosed, the bonnet structure being removably securable to the eye shades using engagement of hook and loop fabric, one of the hook and loop being carried by the eye shades and the other of the hook and loop being carried by the bonnet structure.

22 Claims, 2 Drawing Sheets

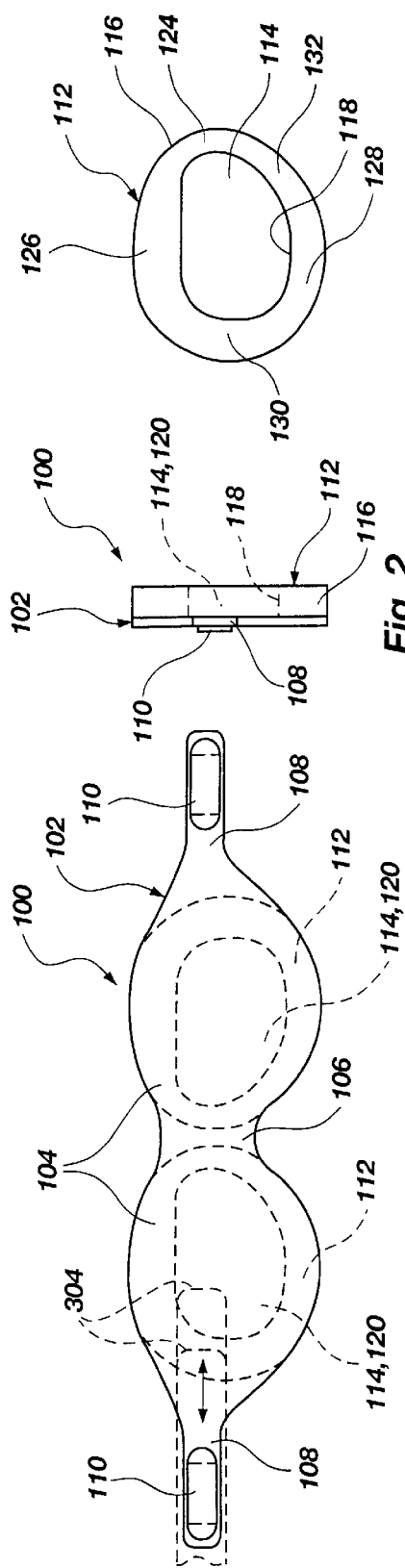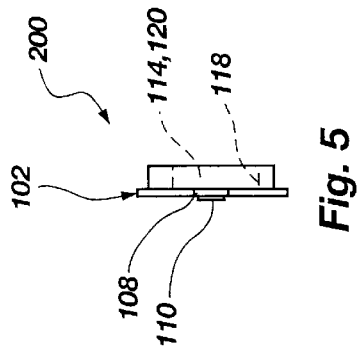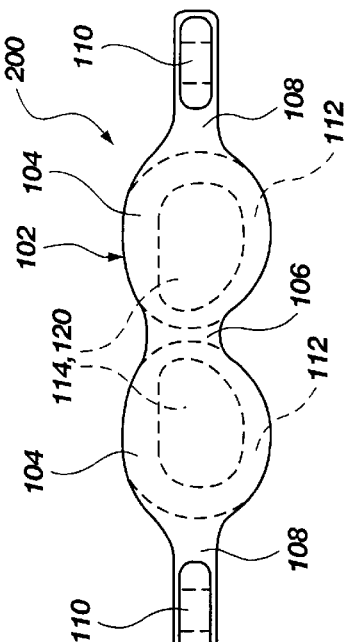

PROTECTIVE EYE SHADES FOR INFANTS AND METHOD OF EYE PROTECTION

BACKGROUND OF THE INVENTION

1. Field of the Invention

This invention relates to eye shades for infants and, most particularly, to infant eye shades that simultaneously preclude exposure of the eyes of an infant to harmful light while substantially eliminating ocular pressure.

2. State of the Art

Certain medical treatments can be harmful to the eyes. For example, children born with jaundice have yellow-colored skin due to the presence of high amounts of bilirubin in the blood. Traditional treatment consists of phototherapy in the form of prolonged exposure to high doses of light, and specifically blue light of 425–470 nm wavelength. While light exposure accelerates the removal of excess bilirubin from the infant's body, it can be harmful to the infant's eyes, especially in the high dosages currently employed.

Ultraviolet light, which is usually incidentally emitted, is known to induce keratitis, conjunctivitis, or lens opacities. Wavelengths of visible light, for example, the broad wavelength range of 400–780 nm including the aforementioned blue light range, and near infrared (780–1400 nm), are known to cause photothermal damage at high levels of irradiance. It has also been suggested that exposure of preterm infants' eyes to even ambient light of high intensity may increase the incidence of retinopathy of prematurity by increasing the toxic effects of oxygen.

Therefore, masks shaped to generally cover the eyes are used during treatment in an attempt to eliminate or reduce the amount of light to the infant's eyes. Many conventional masks are designed to seal light out by cinching a flat, fabric-like covering against the eye. Examples of this approach to infant mask design are disclosed in U.S. Pat. Nos. 4,411,263, 4,502,476, 4,644,588, and 5,613,502. As may be appreciated by those of ordinary skill in the art, snug conformance of the mask material to the infant's head will place direct pressure on the eyeball and eyelid, while a loose-fitting mask leaks light about its periphery and may pose the hazard of occluding the infant's nostrils if slippage of the mask occurs. Thus, existing masks may be uncomfortable because they do not allow the eyelid to move normally and, more significantly, they may cause increased ocular pressure. Further, existing flat mask designs often leak from the side and therefore do not adequately protect the infant's eyes from light. Finally, it has been discovered by the inventor herein that many conventional masks undesirably leak light through the mask material as well.

Thus, it would be advantageous to provide an infant eye shade that does not place direct pressure on the eyeball and eyelid while providing an effective light seal, substantially avoiding ocular pressure and permitting the eyelids to move freely.

BRIEF SUMMARY OF THE INVENTION

An infant eye shade comprising an outer sheath configured as laterally adjacent, generally oval eye cover segments linked by a narrow segment comprising a nose bridge and having tabs flanking the laterally outer edges thereof. Eye rims formed of resilient material of substantial depth or thickness and comprising a border of substantial width about central apertures are adhered to the outer sheath at locations of the oval eye cover segments so that the central apertures are each located over an infant's eye when the eye shades are placed on the infant's head. The eye rims raise the outer sheath material above and out of substantial contact with the infant's eyes, providing chambers to facilitate free and normal movement of the eyes and eyelids located thereunder. The resilient rim material, in combination with the substantial border width of each eye rim, forms a substantially light-tight seal against the infant's skull surrounding the orbit, or eye socket, when the eye shades are secured over an infant's face, at least partially compressing the resilient rim material.

The eye shades of the present invention may be sized and configured for use with premature infants as well as normal term infants of varying sizes. Both the outer sheath and eye rim are fabricated from materials substantially opaque to electromagnetic radiation at least in the form of light wavelengths which may be harmful to an infant's eyes.

The eye shades of the present invention may be secured to an infant's head by a variety of techniques known in the art, including without limitation adhesives, hydrocolloids, gels, nets, straps, or combinations thereof. One exemplary structure for securing the eye shades of the present invention comprises a strap-style bonnet structure which includes an enlarged, central element configured to enhance conformance to an infant's head shape and having straps extending laterally therefrom for respective connection to the tabs of the outer sheath. The strap-style bonnet may be formed of a foam-type material which is both comfortable for the infant and which tends to grip the infant's head to reduce any tendency for slippage as the infant moves. The strap-style bonnet, in combination with the eye shades of the invention, is also contemplated as being within the scope of the present invention.

BRIEF DESCRIPTION OF THE SEVERAL VIEWS OF THE DRAWINGS

FIG. 1 is a frontal elevation of a first embodiment of the eye shades of the present invention;

FIG. 2 is a side elevation of the first embodiment;

FIG. 3 is a frontal elevation of an eye rim employed with the first embodiment of the invention;

FIG. 4 is a frontal elevation of a second embodiment of the eye shades of the present invention;

FIG. 5 is a side elevation of the second embodiment;

FIG. 6 is a frontal elevation of an eye rim employed with the second embodiment of the invention;

DETAILED DESCRIPTION OF THE INVENTION

Figure 7:
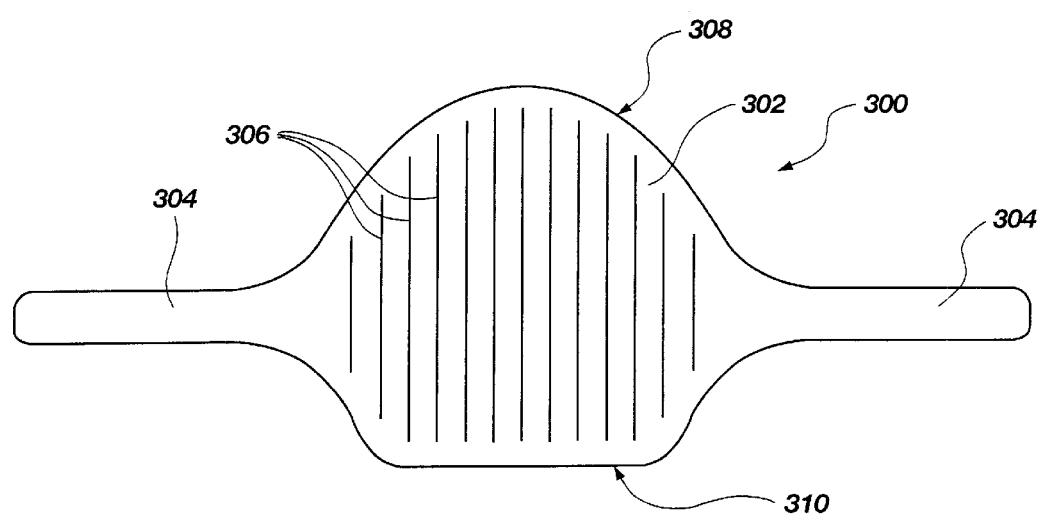
FIG. 7 is a frontal elevation of a bonnet usable with the first and second embodiments of the invention for securing same to the head of an infant.

FIGS. 1 to 3 illustrate a first embodiment 100 of the eye shades of the present invention suitable for use with relatively larger infants, wherein a one-piece, die-cut outer sheath 102 is configured as two generally oval, enlarged eye cover segments 104 linked by a narrower segment comprising nose bridge 106 and having tabs 108 flanking the laterally outer edges thereof Each tab 108 includes a segment 110 of a hook component of a hook-and-loop fabric fastening system adhered to tab 108 at, for example, ends of the segment, preferably by a hypoallergenic adhesive. Velcro® HTH 833 white hook fabric is a suitable fabric, the purpose of which will be explained hereafter in conjunction with FIG. 7 of the drawings.

Outer sheath 102 is formed of a relatively thin material which is soft, opaque to ultraviolet radiation and flexible. By way of example only, a suitable material is a five layer Velcro® brand Veltex® laminate comprising 3900 purple loop fabric, 0.090 inch thick ester charcoal foam, white nonwoven fabric, 0.090 inch thick ester charcoal foam and 3900 black loop fabric. The white, nonwoven fabric of the outer sheath laminate has been found by the inventor herein to be essentially opaque to light in the potentially damaging wavelengths.

Generally oval, or egg-shaped, mirror-image eye rims 112 are adhered to the inner backing of outer sheath 102 over eye cover segments 104 with a hypoallergenic adhesive such as Avery #445 hypoallergenic laminating adhesive and comprise a Velcro® brand laminate of 0.260 inch thick ester foam to Ortho-wick® brand antique gray loop fabric, the eye rims 112 being placed on the outer sheath 102 with the loop material placed on the outside, exposed surface of eye rims 112 which will lie adjacent the infant's face to prevent abrasion thereof. The upper and lower borders of eye rims 112 are substantially coincident with the top and bottom peripheries of outer sheath 102, the locations of eye rims 112 on outer sheath 102 being shown in broken lines in FIG. 1. Each eye rim 112 is sized and configured to lie adjacent an infant's skull surrounding the orbits, or eye sockets, and maintain outer sheath 102 raised above the eyes and eyelids of the infant located within central apertures 114. Further, eye rims 112 are resilient and have a sufficient border width between their outer peripheries 116 and inner peripheries 118 to conform to the topography of the infant's skull and establish a light-tight seal around central apertures 114 while, due to the substantial thickness of eye rims 112, suspending outer sheath 102 above the infant's eyes and eyelids. Thus, the outer sheath 102, in combination with eye rims 112, defines two chambers 120, one over each of an infant's eyes when placed on the infant's head. Referencing FIG. 3, it is noteworthy that the border of each eye rim 112 is thinner along an inner lateral periphery 124 which lies adjacent an infant's nose than at the upper periphery 126, lower periphery 128 and outer lateral periphery 130, where facial skull variances among infants indicate the use of a wider border. Oblique inner periphery 132 lying between inner lateral periphery 124 and lower periphery 128 includes a border of gradually increasing width. Likewise, the border increases in width from the laterally inner extent of upper periphery 126 in a laterally outward (away from nose bridge 106) direction. It is also notable that both inner periphery 118 and outer periphery 116 of eye rim 112 are smooth and defined by a combination of short linear segments in combination with arcuate (preferably radiused) segments to promote maximum flexibility and conformance of the resilient material of eye rim 112 to an infant's skull while precluding wrinkling and folding which might undesirably result in a light leak.

A variety of sizes of eye shades may be employed, as required. The inventor contemplates that three sizes of eye shades may suffice to fit, respectively, preterm infants, most normal term infants, and larger infants. By way of example only, the eye shades of the present invention may, in combination with appropriately sized bonnets 300 as subsequently described herein with respect to FIG. 7, be sized to fit preterm infants with a head circumference of <11 inches (28 cm), smaller infants with a head circumference of 11–13.4 inches (28–34 cm), and larger infants with a head circumference of >13.4 inches (34 cm).

FIGS. 4 to 6 illustrate a second embodiment 200 of the eye shades of the present invention, embodiment 200 being suitable for use with relatively smaller infants, such as the aforementioned preterm infants, also sometimes referred to as "preemies". Eye shades 200 are configured similarly to eye shades 100, and features and elements corresponding to those of FIGS. 1 to 3 are identified in FIGS. 4 to 6 with the same reference numerals. Similarly, the exemplary materials respectively disclosed as suitable for use as outer sheath 102 and eye rims 112 of eye shades 100 are equally suitable for use with eye shades 200. The only significant differences between eye shades 100 and eye shades 200 are in a smaller overall length of eye shades 200 and smaller-dimensioned eye cover segments 104 in combination with smaller eye rims 112. In other words, different sizes of the eye shades of the present invention are similar in configuration, but proportionally larger or smaller, as required to fit the infant.

As noted above, the eye shades of the present invention may be secured to an infant's head by a variety of techniques known in the art, including without limitation adhesives, hydrocolloids, gels, nets, straps, or combinations thereof. Thus, if hook fabric segments 110 are not employed, tabs 108 may be coated with adhesive, a hydrocolloid, or a gel. Similarly, tabs 108 may comprise a portion of a net or strap to be placed over the infant's head in use.

FIG. 7 discloses one preferred structure for securing the eye shades of the present invention in place over an infant's eyes in the form of a strap-style bonnet 300 which includes an enlarged element 302 configured to enhance conformance to an infant's head shape. The strap-style bonnet 300 may be formed of a foam-type material which is both comfortable for the infant and which tends to grip the infant's head to reduce any tendency for slippage as the infant moves. One suitable material is the aforementioned material of outer sheath 102, die cut to shape. The enlarged element 302 is located at the midsection of the bonnet 300, straps 304 extending laterally and equidistantly from enlarged element 302. Enlarged element 302 includes a plurality of slits 306 therethrough, oriented transversely to an axis along which straps 304 lie. The upper periphery 308 of enlarged element 302 is arcuate, generally semicircular and of substantial radius, and extends upwardly from straps 304. The lower periphery 310 of enlarged element 302 extends downwardly from straps 304, and a majority of lower periphery 310 lies substantially parallel in orientation to the axis along which straps 304 lie. The edges of straps 304 extend smoothly and arcuately into upper and lower peripheries 308 and 310 of enlarged element 302. In use, the outer end of each strap 304 is extended about the infant's head from the rear thereof whereon enlarged element 302 has been placed, over hook fabric segment 110 on tab 108 of the outer sheath 102 so that the loop material of the inner surface of outer sheath 102 engages the hooks of hook fabric segment 110. Thus, as shown in broken lines in FIG. 1, straps 304 may be extended over hook fabric segments 110 to adjust the circumference of the eye shades 100 or 200 in combination with bonnet 300 to the diameter of the infant's head for a snug but comfortable fit. When placed on an infant, enlarged element 302 will rest on the occipital bone at the rear of the infant's skull and slits 306 in combination with the combined configurations of upper periphery 308 and lower periphery 310 permit enlarged element 302 to "cup" somewhat as the slits 306 laterally enlarge or open (see FIG. 8), permitting enlarged element 302 to conform to the skull and the notch at the lower rear thereof, preventing, in combination with the material of bonnet 300, slippage of the bonnet 300 and eye shades 100 or 200. As with the eye shades of the present invention, bonnet 300 may be sized upwardly or downwardly as required to accommodate, in combination with appropriately sized eye shades, a particular infant.

Figure 8:
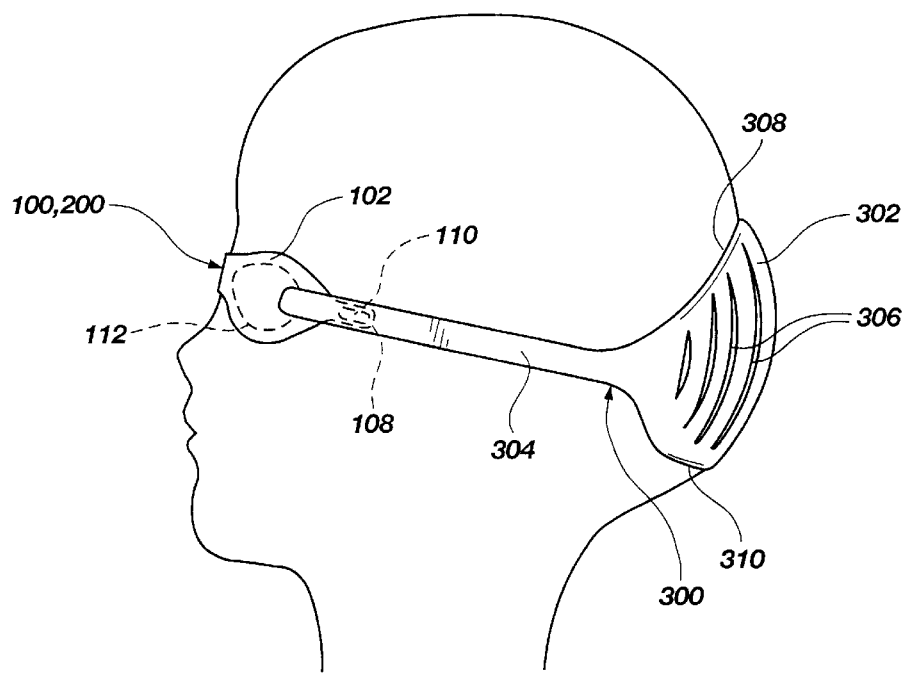
FIG. 8 is a side view of an infant wearing eye shades according to the invention.

FIG. 8 of the drawings shows eye shades 100 in combination with bonnet 300 placed on an infant's head for phototherapy.

While the present invention has been described and illustrated in terms of certain specific embodiments, those of ordinary skill in the art will understand and appreciate that it is not so limited. Additions to, deletions from and modifications to these specific embodiments may be effected without departing from the scope of the invention as defined by the claims. Furthermore, features and elements from one specific embodiment may be likewise applied to another embodiment without departing from the scope of the invention as defined herein.

What is claimed is:

1. Protective eye shades for an infant, comprising:
   an outer sheath including two enlarged, laterally adjacent segments; and
   two rims, each comprising a resilient material defining a border substantially encompassing a central aperture and each being of substantial thickness so as to project from the outer sheath and, in combination with a surface of the outer sheath, define a chamber, each rim being secured to one side of the outer sheath over an enlarged segment.

2. The protective eye shades of claim 1, further comprising a bonnet structure secured to the outer sheath proximate the enlarged segments and sized and configured to maintain the protective eye shades on the head of the infant with the apertures placed over eyes of the infant.

3. The protective eye shades of claim 1, wherein the rims are each of substantial thickness so as to project from the outer sheath and, in combination with a surface of the outer sheath, define a chamber.

4. The protective eye shades of claim 3, wherein the rims each comprise a resilient material defining a border about the central aperture.

5. The protective eye shades of claim 1, wherein the rims and the enlarged segments of the outer sheath are of substantially the same size and outer peripheral configuration at upper and lower edges thereof.

6. The protective eye shades of claim 1, wherein the rims are substantially oval shaped, and an inner lateral periphery of each rim includes a thinner border than a remaining portion of each rim.

7. The protective eye shades of claim 1, wherein the rims comprise a laminate of a resilient material to a loop fabric, and the rims are secured to a surface of the outer sheath with the loop fabric facing away from the outer sheath.

8. The protective eye shades of claim 1, wherein the rims project at least about one quarter of an inch from the outer sheath.

9. The protective eye shades of claim 1, further including structure for securing the outer sheath over a face of the infant with the apertures of the rims over the infant's eyes, the structure for securing comprising at least one of a net and a strap.

10. Protective eye shades for an infant, comprising:
    an outer sheath including two enlarged, laterally adjacent segments;
    two rims, each comprising a border substantially encompassing a central aperture, each rim being secured to one side of the outer sheath over an enlarged segment; and
    a bonnet structure secured to the outer sheath proximate the enlarged segments and sized and configured to maintain the protective eye shades on the head of the infant with the apertures placed over eyes of the infant;
    wherein the outer sheath further includes a tab extending laterally from each enlarged segment, the bonnet structure includes a strap element end extending over each tab, and the strap element ends are each secured over a tab of the outer sheath.

11. The protective eye shades of claim 10, wherein each tab carries a segment of hook fabric thereon, the strap element ends each comprise a loop fabric, and the hook fabric segments engage the loop fabric to secure the bonnet structure to the outer sheath.

12. The protective eye shades of claim 10, wherein the bonnet structure includes a central, enlarged element having a strap element extending laterally from each side thereof.

13. The protective eye shades of claim 12, wherein the enlarged element includes an arcuate upper periphery, a lower periphery including a substantially linear portion substantially parallel to the laterally extending strap elements, and a plurality of mutually laterally adjacent slits therethrough oriented substantially transverse to the laterally extending strap elements.

14. The protective eye shades of claim 13, wherein the outer sheath is formed of a fabric laminate comprising at least one layer being substantially opaque to wavelengths of light potentially harmful to the eyes of the infant.

15. Protective eye shades for an infant, comprising:
    an outer sheath comprising a laminate of at least one layer of loop fabric and at least one layer of foam, and including two enlarged, laterally adjacent segments; and
    two rims, each comprising a border substantially encompassing a central aperture, each rim being secured to one side of the outer sheath over an enlarged segment.

16. The protective eye shades of claim 15, further including a bonnet structure for securing the outer sheath over an infant's eyes, removably secured to one of a hook or loop fabric on a surface of the outer sheath by engagement thereof with the other of a hook and loop fabric on the bonnet structure.

17. The protective eye shades of claim 16, wherein the bonnet structure includes an enlarged element thereon located for placement over a rear portion of a skull of an infant wearing the protective eye shades, at least the enlarged element of the bonnet structure having an inwardly facing surface selected to prevent slippage thereof on the skull and being configured and structured to enhance conformance thereof to a shape of the rear portion of the skull.

18. The protective eye shades of claim 17, wherein the bonnet structure includes straps laterally extending from the enlarged element, each strap having a loop fabric surface at least adjacent an outer end thereof.

19. The protective eye shades of claim 18, wherein the straps each extend over a tab of the outer sheath laterally adjacent an enlarged segment, and wherein the outer end of each strap having the loop fabric surface engaging a hook fabric segment disposed on a tab of the outer sheath.

20. The protective eye shades of claim 19, wherein a circumference of the outer sheath and bonnet structure, in combination, is adjustable by engagement of different portions of the loop fabric surface of at least one of the straps to at least one hook fabric segment.

21. Protective eye shades for an infant, comprising:
    an outer sheath including two enlarged, laterally adjacent segments; and two rims, each comprising a border substantially encompassing a central aperture, each rim being secured to one side of the outer sheath over an enlarged segment, further including structure for securing the outer sheath over a face of the infant with the apertures of the rims over the infant's eyes, the structure for securing comprising at least one of an adhesive, a hydrocolloid, and a gel.

22. A method of protecting the eyes of an infant during phototherapy while permitting substantially free movement of the infant's eyelids, comprising:

providing eye shades comprising an outer sheath having two resilient rims projecting therefrom and surrounding apertures closed on one side by the outer sheath;

placing the eye shades over the face of the infant with each aperture over an eye of the infant with the resilient rims at least partially compressed to conform to the skull of the infant surrounding each eye and the outer sheath extending over each eye and substantially supported thereover by the resilient rims.

* * * * *